United States Patent
Hufe et al.

(10) Patent No.: US 6,354,737 B1
(45) Date of Patent: Mar. 12, 2002

(54) DIGITAL IMAGE ORIENTATION MARKER

(75) Inventors: Mark J. Hufe; David Paul Wolff, both of Newark; Chuande Liu, Hockessin, all of DE (US)

(73) Assignee: Direct Radiography Corp., Newark, DE (US)

(*) Notice: Subject to any disclaimer, the term of this patent is extended or adjusted under 35 U.S.C. 154(b) by 0 days.

(21) Appl. No.: 09/438,606

(22) Filed: Nov. 12, 1999

(51) Int. Cl.[7] .............................................. H05G 1/28
(52) U.S. Cl. ..................... 378/205; 378/163; 378/164; 378/165; 235/462.01
(58) Field of Search ................................ 378/205, 163, 378/162, 164, 165, 170, 206, 207; 235/23, 462.01

(56) References Cited

U.S. PATENT DOCUMENTS

| | | | |
|---|---|---|---|
| 4,127,774 A | * 11/1978 | Gillen | 378/165 |
| 4,698,836 A | * 10/1987 | Minasian | 378/165 |
| 5,051,904 A | * 9/1991 | Griffith | 378/23 |
| 5,070,454 A | * 12/1991 | Griffith | 378/163 |
| 5,077,778 A | * 12/1991 | Fabian | 378/165 |
| 5,123,040 A | * 6/1992 | Fabian | 378/165 |
| 5,189,689 A | * 2/1993 | Fabian | 378/165 |
| 5,254,480 A | 10/1993 | Tran | 437/2 |
| 5,315,101 A | 5/1994 | Hughes et al. | 250/208.1 |
| 5,319,206 A | 6/1994 | Lee et al. | 250/370.09 |
| 5,563,421 A | 10/1996 | Lee et al. | 250/580 |
| 5,648,660 A | 7/1997 | Lee et al. | 250/370.09 |
| 5,773,832 A | 6/1998 | Sayed et al. | 250/370.09 |
| 5,804,832 A | 9/1998 | Crowell et al. | 250/580 |

* cited by examiner

Primary Examiner—Drew Dunn
(74) Attorney, Agent, or Firm—Ratner & Prestia

(57) ABSTRACT

An orientation marker for a digital radiogram formed by a plurality of pixels arrayed along a plurality of rows and columns. The pixels have densities which represent the radiogram optical density at each pixel point, and the densities are represented by digital values. The marker is made by a number of marker pixels arrayed along at least one row and one column of the radiogram. Each of the pixels forming the marker, have a marker pixel digital value which has been selected to form an asymmetrical marker pixel pattern on the radiogram, replacing the original radiogram pixel values.

13 Claims, 5 Drawing Sheets

DIGITAL IMAGE ORIENTATION MARKER

BACKGROUND OF THE INVENTION

1. Field of the invention

This invention relates to digital radiographic image displays and more particularly to the use of an asymmetrical marker to determine the proper orientation of a displayed digital radiogram.

2. Description of Related Art

In the past decade there has been great progress made in the area of direct radiographic imaging using detectors comprising a two dimensional array of minute sensors to capture a radiation generated image. Information representing an image is captured, often as a charge distribution stored in a plurality of charge storage capacitors in individual sensors arrayed in a two dimensional matrix. We will refer to such detectors generically as direct radiographic detectors to differentiate them from the often referred to as traditional radiographic detectors which employ a photosensitive film usually in combination with an intensifying screen to produce a photographic image of the incident X-ray radiation.

The direct radiographic detectors typically comprise a two dimensional array of sensors with associated switching and addressing circuitry built on an insulating substrate, usually a glass plate. U.S. Pat. No. 5,319,206 issued to Lee et al. on Jun. 7, 1997, shows a typical direct radiation detector comprising an array of sensors for the generation and capture of charges following exposure to X-ray radiation. Readout of the stored charges is accomplished in any one of a plurality of manners. U.S. Pat. No. 5,648,660, also by Lee et al. discloses a method for the readout of stored charges in a direct radiographic imaging panel.

Direct radiation detectors offer a number of distinct advantages over the traditional film methods. The availability of a radiogram in electronic signal format, permits the use of digital signal conversion and all the advantages of signal storing, retrieval, transmission and processing associated with digital imaging.

This availability of the image in digital format, however, at times presents certain problems. For instance a captured digital image is stored in the form of a plurality of pixel values. These values undergo a number of operations as part of the system image processing routines, and such operations often include image rotation to present the image in "portrait" or "landscape" format for instance and may involve in addition to rotation, image mirroring, a process where the image is "flipped" front to back.

While this versatility presents a number of advantages, it is important to be always able to determine the original image orientation and original pixel location. This is particularly important when bad pixel correction must be applied. Such correction relies on pixel maps that correspond to the original image capture orientation as it applies corrections to the pixels corresponding to predetermined exact coordinates of detector elements. If the orientation of the image to be corrected is not the original, mapped bad pixels will not correspond to rotated image pixels.

A second reason for the need to know the original orientation of a radiogram is that when viewing a radiogram, such as a chest image, it is essential to know if the image has been flipped or not, as this places the internal organs in their proper position. This is important because a small minority of the population has their heart and other organs on the opposite side from the majority, i.e. heart is center right rather than center left, etc. The radiologist must be able to determine whether the displayed image has been mirrored or not, so that he knows whether he is looking at a front or a back view of the patient.

In traditional radiography this was done by physically marking one side of the film, such as by notching a corner of the film, or placing a piece of tape at one corner on one side of the film. This, however is not practical when there is no film present and the image is a sequence of a plurality of numbers stored in a memory. There is thus a need to develop a marker for a digital radiogram that will permit the easy identification of the image orientation at any stage of processing and display relative to the original image orientation as captured by the direct radiographic detector.

SUMMARY OF THE INVENTION

It is, therefore, an object of this invention to provide an orientation marker for a digital radiogram comprising a plurality of pixels arrayed along a plurality of rows and columns, the pixels having densities represented by digital values. The marker comprises a number of marker pixels arrayed along at least one row and one column. Each of these pixels has a marker pixel digital value which has been selected to form an asymmetrical marker pixel pattern on the radiogram. Preferably, the marker pixel values replace the original radiogram pixel values.

The desired asymmetry may be obtained in one of two manners or as is preferred by a combination of the two manners. It can be obtained by selecting the marker pixel digital values to form a unique, asymmetrical sequence of values that can only be retrieved (or its density pattern observed) when the digital values representing the radiogram are retrieved (or displayed) in a particular orientation, such orientation being almost always, the original orientation of the radiogram and corresponding image data. The marker asymmetry may also be obtained by the use of a particular selected marker geometry or as preferred, by a combination of pixel geometry and distinct values such as to obtain the desired asymmetry in readout and display of the marker which identifies the radiogram original orientation.

In order for the marker not to intrude in the diagnostic portion of the radiogram, the marker is preferably placed adjacent an upper left hand corner of the digital radiographic image. Still more preferably the marker may be shaped as an "L" having a pixel common to a row and a column of the rows and column comprising the marker, and the marker common to both such row and column is a first pixel on a first row and a first column of the plurality of rows and columns of pixels forming the radiogram.

Viewed in a different way, the invention is an orientation marker comprising a number of marker pixels in a two dimensional array superposed on a digital radiogram comprising a plurality of pixels having digital values representing pixel densities. Each of the marker pixels has a value selected to form in combination with all the other marker pixel values a machine readable identification code when the digital values representing the radiogram (with the marker included) are read out to process the image data or to display the radiogram in its original orientation as captured by the detector.

This invention may also be viewed as a plurality of digital values representing a radiogram each of said digital values corresponding to a pixel arrayed along a plurality of rows and columns and representing said pixel density. A selected number of said digital values have imposed values selected to together, form a machine readable identification code when the radiogram digital values are read in an desired radiogram orientation.

The invention also comprises a process for identifying the proper orientation of a digital radiogram composed of a plurality of pixels each having a digital value representing image densities. According to this process a digital marker is placed on the captured digital radiogram by:

a) selecting a plurality of pixels along at least one row and at least one column to form an array of selected pixels;

b) selecting a plurality of digital pixel values c) replacing the digital values of the plurality of selected pixels with the selected digital values to form an asymmetrical array of marker pixels.

BRIEF DESCRIPTION OF THE DRAWINGS

The invention can be more fully understood from the following description thereof in connection with the accompanying drawings described as follows.

FIG. 2 shows a preferred marker shape and placement in accordance with the present invention.

FIGS. 3 through 5 show alternate marker designs and placement also in accordance with the present invention.

DESCRIPTION OF THE PREFERRED EMBODIMENT(S)

Figure 1:
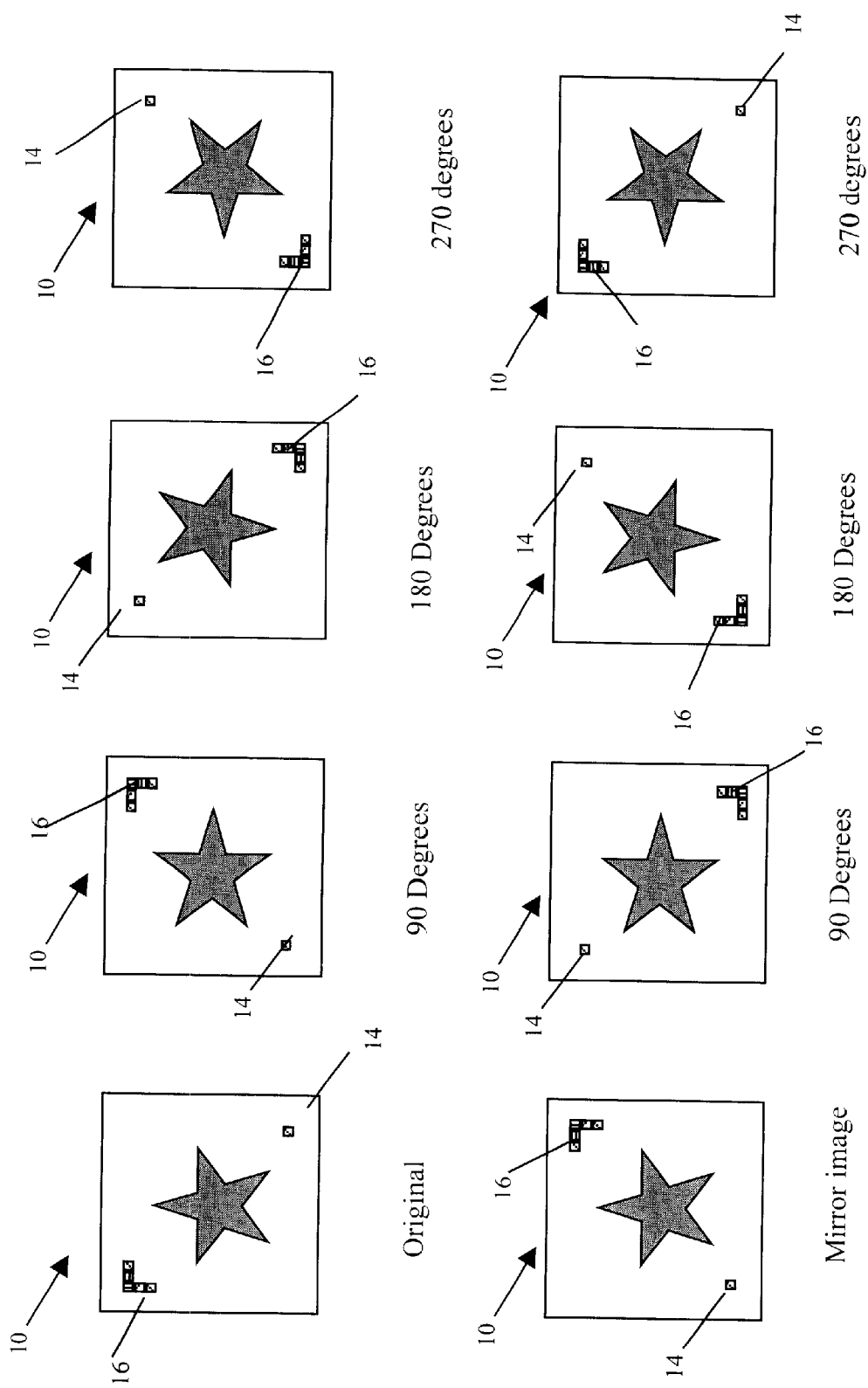
FIG. 1 shows a schematic representation of a digital radiogram as it undergoes 360 degree rotation and left to right translation (mirror image display or mirroring)

Throughout the following detailed description, similar reference characters refer to similar elements in all figures of the drawings.

The invention is applicable to any digital radiographic system wherein the radiogram is represented by a plurality of stored digital values. Typical such systems employ a digital detector which can be any one of a plurality of known radiographic detectors capable of generating an electrical signal representing impinging radiation intensity variations. Such radiographic detectors are described inter alia in U.S. Pat. No. 5,773,832, issued Jun. 30, 1998 to Sayed et al., U.S. Pat. No. 5,254,480, issued Oct. 19, 1993 to Nang T. Tran, or U.S. Pat. No. 5,315,101, issued May 24, 1994 to Hughes et al. In addition the invention is equally applicable where the digital radiogram is the result of digitization of a traditional film radiogram. Such digitization process is well known in the art and involves scanning a film radiogram and converting it into digital values.

In the present description of the invention, we will refer for illustration purposes to a specific detector which is a preferred detector contemplated for use in the present invention. This is a direct conversion radiation detector of the type disclosed in the aforementioned U.S. Pat. No. 5,648,660 by Lee et al. As disclosed in this patent the detector comprises a two dimensional array of individual radiation sensors on a supporting dielectric base forming a panel of appropriate size, usually 14 by 17 inches. The panel is enclosed in an enclosure such as disclosed in U.S. Pat. No. 5,804,832 issued to Crowell et al. The sensors each comprise a charge storage capacitor and a switching transistor adjacent the capacitor. Conductive lines extend in the spaces between sensors and the source and gate electrodes of the switching transistors are connected to the conductive lines along individual columns and rows.

A photoconductive layer is placed over the individual sensors and a biasing electrode is placed over the photoconductive layer. Charge blocking layers may be placed on one or both sides of the photoconductive layer. Upon exposure to radiation, electron and hole pairs are freed in the photoconductive layer. Under an imposed static magnetic field, electrons migrate to the biasing electrode and holes to the charge storage capacitor (depending on the polarity of the applied field).

Following exposure the biasing field is removed and the accumulated charge in the individual sensors is read out, amplified, digitized and stored. The panel is next reconditioned for the next exposure, by exposing to illuminating radiation as disclosed in U.S. Pat. No. 5,563,421 issued to Lee et al. Preferably between exposures the radiation detection panel is continuously cycled between a state where the biasing voltage is zero and a state where a biasing voltage other than zero is applied to the biasing electrode followed by image readout even when no exposure has occurred. This is referred to as the standby state, as distinguished from the ready state in which the cycling has been interrupted and a proper biasing voltage has been applied to the sensors.

The charge obtained from the sensors produces an analog electrical signal which is amplified and digitized. This digital signal represents the raw digital data output of the panel. The raw digital data is subjected first to a gain pixel equalization process and then to a bad pixel correction process. Typically, gain equalization involves applying a pre-calculated gain factor, usually available in a look up table (LUT), to each digital pixel value to compensate for gain non uniformity in the individual sensors. The bad pixel correction follows and entails the replacement of previously identified and mapped bad pixels by a value calculated by averaging 8 adjacent pixel values from the immediate surrounding pixels.

Referring next to FIG. 1, there is shown a stylized radiogram 10 which includes an image 12. The image 12 may for instance represent a frontal lung shot. Radiogram 10 in FIG. 1 is shown in a number of orientations, beginning with the original orientation of the radiogram as originally captured and followed from left to right by a first, second and third 90 degree rotations. The second line of radiograms shows the same original radiogram after it has been mirrored and again as it is rotated through 270 degrees in 90 degree increments.

The radiogram representation in FIG. 1 also includes two types of identifier markers, a first marker 14 which is shown near the bottom right hand corner of the original radiogram, and a second marker 16 shown at the upper left hand corner of the original radiogram.

In studying FIG. 1, first ignore the presence of both markers. In the absence of any markers it is often impossible to tell with certainty whether the radiographic image displayed is the original or a mirror image. Therefore, a doctor viewing the radiogram will be unable to identify whether the image he views was taken with the patient facing the x-ray unit or with his back to it, and as result whether a point of interest is on the right lung or the left lung for instance.

Furthermore, because during use digital radiographic detectors tend to develop bad pixels that are not part of the original bad pixel mapping operation, operators often display a blank field exposure to see if there have developed any bad pixels which are not included in the original pixel map for the detector, and are thus uncorrected. For this process, it is essential that actual location of the bad pixels be accurately determined. If the image has undergone rotation, the bad pixels no longer appear at the original co-ordinates as viewed by the operator.

Simply placing a marker such as symmetrical marker 14, does not solve the problem. Observe the location of the marker in FIG. 1 in the original image and also in the mirrored image that has been rotated 270 degrees. Both appear in identical format at the bottom right hand corner of the image, generating uncertainty as to the proper image orientation.

Figures 2, 3:
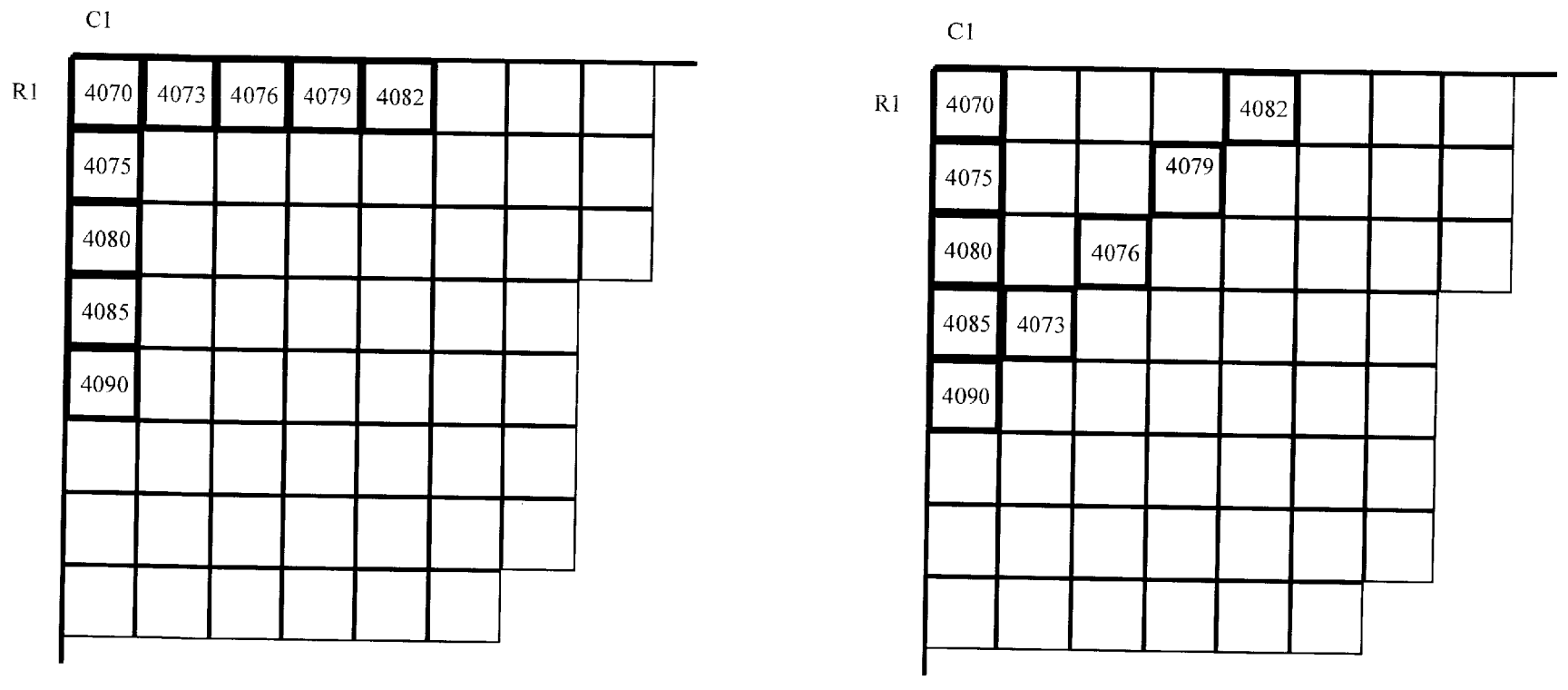

The marker identified as marker 16, on the other hand avoids any such uncertainty. FIG. 2 shows an enlarged marker similar to marker 16. As shown, marker 16 is an asymmetrical marker, meaning that it is composed from a plurality of different value pixels arranged so that they present a particular sequence of numbers only when read out from left to right and top to bottom of a pixelated rasterized image represented as a plurality of digital values each digital value representing a corresponding pixel density.

In the example illustrated in FIG. 1 the marker 16 is composed of five pixels. Three are along a row of pixels and three are along a column. One pixel is common to both the row of pixels and the column of pixels. In accordance with the present invention, the marker is made from a selected plurality of pixels having specific digital values, which have been decided when at the marker design stage. These different pixel values replace the pixel values in the original image when the marker is inserted in the image data.

In FIG. 1 the different digital values are shown as different fill patterns representing the different densities corresponding to each of the marker pixel digital values. Once the marker has been placed in the image data, it follows the image data through any mirroring or rotation that may be applied to the data. As shown in FIG. 1 rotating the image through 270 degrees does not produce any situation where the marker can be read out to produce the same sequence of digital values as in the original image, and this difference is also observed visually.

Mirroring of the image and subsequently rotating by 270 degree places the marker at the same location as in the original image, however as can be seen in FIG. 1, the pixel density sequence when readout from left to right is different from the pixel density sequence in the original when readout from left to right. Observation of the marker in all possible positions shows that there is one and only one image orientation that will produce a readout (or display) of the marker with the proper density value sequence.

Thus the orientation of the image is always correctly identified following any rotation or mirroring of the data, without need to keep track of previous rotations or mirroring operations on the data.

FIG. 2 shows a preferred marker and its location in the image data. The marker consists of a plurality of 9 pixels arrayed along a row and a column of the digital data representing the densities of the pixels in the rows and columns of the radiogram, preferably along row R1 (the first image pixel row) and C1 (the first image pixel column) each having a digital value that is different from all other marker pixel values. Typical digital values are given in the figure for a 12 bit system of digital values having 4096 digital values. (0–4095). Use of an extreme range in the selection of values provides the highest probability that the selected values will be outside the normal image values.

It often the practice in image processing in this field to compress the raw digital data output of the panel from 14 bits to 12 bits. One way to achieve this is through a linear to log transformation of the raw digital data. In such case, if the marker is inserted in the data prior to the transformation, the linear values chosen for the marker must not only be unique but must also survive the transformation. What happens during the log conversion and transformation to 12 bits is that the values at the high end of the 14 bit scale get squashed into fewer values in the 12 bit scale. For example, if the following values are selected in the 14 bit domain, 16381, 16382, 16383 as three unique values for three marker values, they all get transformed to the same log value, 4095. It is thus important select 14 bit linear values sufficiently far apart that the values are still unique when transformed to 12 bit domain.

Figure 5:
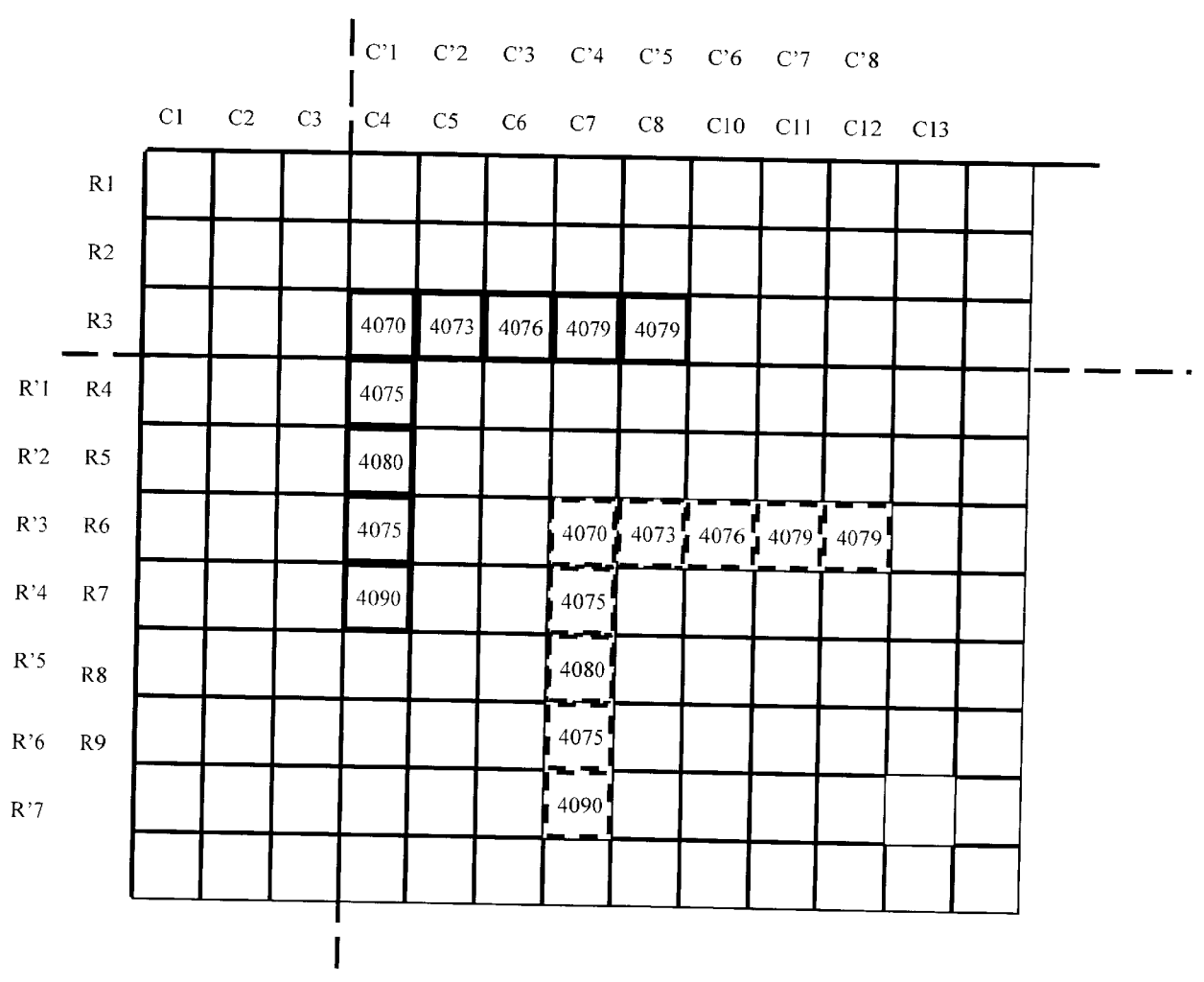

FIGS. 3 to 5 show alternate embodiments and placement for the marker. As shown in FIG. 4 the marker pixels 22 need not be adjacent pixels. As shown in FIG. 5 the marker 20' need not be placed in the uppermost left hand corner of the pixel array. Further more the selected values need not all be different for each of the pixels of the marker, even though different digital values are preferred. What is important is that the combination of marker shape and marker pixel values produce an asymmetrical marker as defined above.

While it is contemplated that the marker will be placed in the image data by replacing a number of image data pixels with the selected values for the marker, the marker can also be created by adding the selected marker pixel values to the underlying image pixel values at the location where the marker is placed. While this method is not particularly desirable when it is primarily contemplated that the orientation of the image will be done automatically with a computer reading out and identifying the marker pixels, this method may be preferred when visual identification is contemplated since it results in a superposed image whose density is above the neighborhood pixel density and therefore easier to identify visually.

Figure 6:
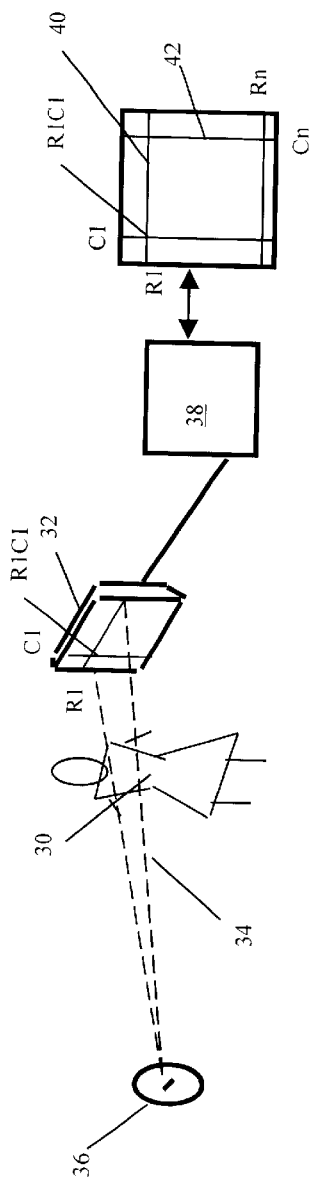
FIG. 6 shows a typical setup for exposing a radiogram using a digital radiographic detector helpful in explaining the term proper image orientation used in this description.
Figure 7:
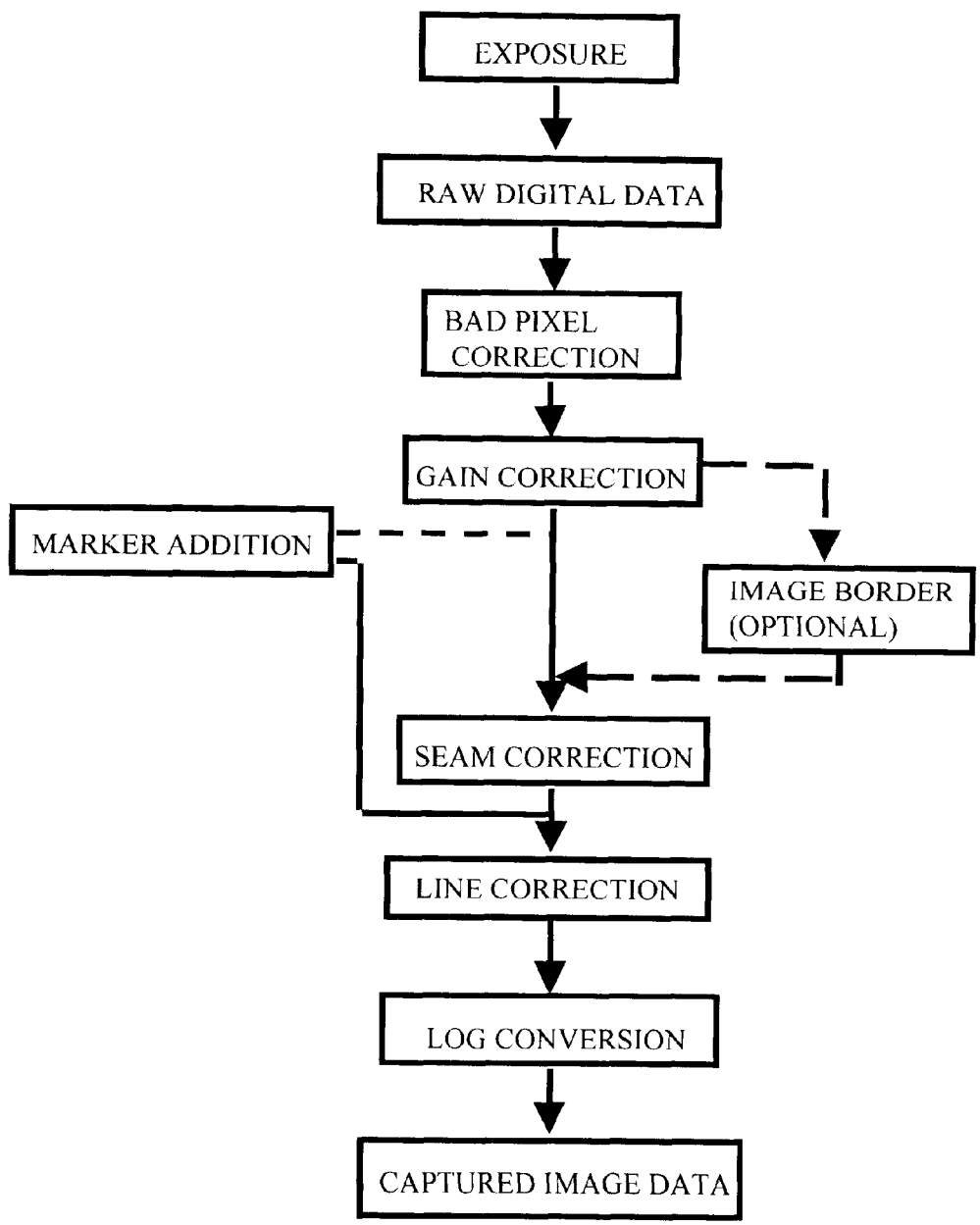
FIG. 7 shows the typical process step sequence for retrieval and display of the radiographic data representing a radiogram and the marker addition according to the present invention.

FIGS. 6 and 7 respectively, show a typical radiation exposure setup and the process steps involved in capturing and tagging a radiogram using the marker of the present invention.

As shown in FIG. 6 a patient 30 is placed in front of the digital radiation detector 32 in the path of an x-ray radiation beam 34 emanating from a source of radiation 36. The digital detector is controlled through a controller 38 which typically includes at least a programmed computer with associated memory for controlling the functions of the detector and recovering the data captured by the detector as a result of a radiation exposure of the patient.

In the preferred embodiment, where a detector of the type discussed earlier in the specification is used, typically, the controller will cycle the digital detector through a number of cycles, one of which will be the actual exposure of the patient. The analog signal stored in the detector storage capacitors is retrieved and converted to a digital signal. This signal undergoes an initial signal processing to remove noise information. The resulting digital signal is the raw image digital signal.

As illustrated, following exposure the signals representing the image are stored in a manner that maintains the individual pixel order along rows 40 and columns 42 of the detector in a memory 44. This is what is referred to as the original orientation.

Typically, in handling image data, the data is read out of the storage memory beginning with the first pixel of the first row and first column (R1C1), and proceeds from left to right and top to bottom (as the image will be viewed) along the first row to the last pixel of the first row and last column (R1Cn) then continues with the second row and so on to the last row and last column. When the data undergoes a 90 degree rotation, for instance, the original pixel value for R1C1 is placed in the location of R1Cn, and the original pixel from location RnC1 becomes pixel R1C1, and so on. Similarly in a mirroring situation, pixel R1Cn becomes pixel R1C1 and so on. Thus when in this specification we refer to original image (or data) orientation we refer to the stored or displayed data where if readout from left to right and top to bottom, the R1C1 pixel of the panel capturing the image appears in the R1C1 position.

The original raw data, as shown in FIG. 7, is next subjected to bad pixel correction and gain correction. Following gain correction an image border may optionally be added comprising setting the pixel values along a few rows and columns around the perimeter of the image to a preset value. When the digital detector consists of a plurality of smaller size detectors that have been tiled together to form a larger unit, as is sometimes the case, there is an additional step performed to correct any image loss or distortion arising at the vicinity of the seam between the panels forming the larger detector.

The orientation marker according to the present invention is, preferably, added either before or after the seam correction step. The orientation marker may also be added after a line correction of the image data (a process for correcting a series of bad pixels forming a line, described in co-pending patent application ser. No. 09/255.772 assigned to the assignee of the present invention) and a log conversion of the original image data values used to convert such values from 16 bits to 12 bits.

All of the above operations are performed on the original image data right after it is captured by the digital detector and before any mirroring or rotation of the image occurs. The resulting data is the captured image data and includes the marker according to the present invention. Any subsequent image rotation will also rotate the marker which now forms an integral part of the image.

In actual use it is often desirable to crop a radiogram. Such cropping may be done in at least two places during the process of image acquisition and display. The image may be cropped as it is received from the detector while it is still raw image data, or it may be cropped at a later stage after it has been processed and become what we have referred to as captured image data. In the first instance there is no problem regarding the placement of the marker since the marker is placed in the image after cropping the image. In the second and most likely instance, the cropping process is likely to remove the marker together with the unwanted information in the radiogram, particularly if the marker has been placed close to or at the border of the radiogram.

It is therefore still within this invention to provide moving the marker whenever cropping occurs from an area of the radiogram cropped to a corresponding area of the cropped radiogram. For example, once the pixels to be cropped have been identified in the captured image data, these pixels are tested for the presence of marker pixels. If marker pixels are identified as being within the cropped pixels the complete marker is relocated to an equivalent position in the new image frame by replacing the image pixels with the marker pixels. For example, the marker shown in FIG. 5 is occupying the pixels identified as R3C4, R3C5, R3C6, R3C7, R3C8, R4C4, R5C4, R6C4 and R7C4. A proposed image cropping along the dotted lines, involves eliminating columns C1 to C3 and rows R1 to R3, pixels R3C4, R3C5, R3C6, R3C7, R3C8, will be identified as cropped pixels belonging to the marker.

Marker pixel identification may be done by examining the full sequence of the marker pixels to determine whether any as in this example, intrude in the cropped area. Once this has been determined the marker is moved completely to a corresponding position in the new image generated as a result of the cropping. In the example illustrated in FIG. 5, pixel R4C4 becomes pixel R'1C'1 in the cropped image. Therefore original marker pixel R3C4 with the marker value 4070 is moved to replace the pixel value in position R6C7 of the original image, and the rest of the marker pixels replace the old image pixel values in R6C8, R6C9 . . . . R7C7, R8C7 etc.

In situations as in this example, there may be left in the new, cropped image, a number of the old marker pixels. In this example original pixels R4C4, R5C4, R6C4 and R7C4 remain in the new image, in new locations R'1C'1, R'2C'1, R'3C'1 and R'4C'1. These marker pixel values may be left as they are, or they may be replaced by an extrapolated image pixel value from a neighborhood of adjacent, image pixel values.

The invention has been described with reference to a specific detector embodiment and a particular initial image processing sequence which is associated with the particular sensor used. This is, however, done in order to illustrate the invention and is not intended to limit it to the particular radiation detection system and image correction used. Furthermore, the invention has been described with reference to an original image orientation as defined herein above. However the invention is equally applicable to any desired orientation, and such desired orientation does not have to be the original orientation as defined. For example, an image without any orientation identification may be received and the orientation in which this image is received may be preserved by the application of a marker as hereinabove described. Or a particular image orientation may be desired to be preserved, in which case a marker may be applied to preserve such desired orientation.

The above described creation of a marker according to this invention is preferably implemented by software for programming a computer, typically the computer used to process the raw data obtained from the detector. Such program may be embodied in a program storage device readable by machine, tangibly embodying a program of instructions executable by the machine to perform a set of method steps necessary to implement the above described program. Such program storage device may be a floppy disk, a CD ROM disk, a magnetic tape medium, an internal computer memory, or any other medium or device capable of storing information readable by the computer. It may be a free standing program or it may be a portion of a larger program executable by the computer.

Such program will contain the needed steps to identify the data representing the radiogram, and will include the required routines and subroutines to retrieve and apply a set of values and their intended location in the radiogram and to replace the raw data values on the radiogram by the retrieved marker values. The set of values may be a part of the program or may be stored in a separate memory and accessed by the program. In the alternative such program will have the ability to add the selected values to the raw data values. In a further embodiment such program will include routines and sub-routines to identify any cropped rows and columns and to reposition the marker values to new rows and columns corresponding to the original, cropped rows and columns in the cropped radiogram. This type of programming is uncomplicated and the technology to implement it well known in the art.

The person skilled in the art will recognize that other similar systems may benefit from implementation of this our invention and such application is within the scope of our invention which we claim:

What is claimed is:

1. An orientation marker for a digital radiogram comprising a plurality of pixels arrayed along a plurality of rows and columns, the pixels having densities represented by digital values, said marker comprising a number of marker pixels arrayed along at least a row and a column, each of said marker pixels having a marker pixel digital value selected to form an asymmetrical marker pixel pattern on said radiogram.

2. The orientation marker according to claim 1 wherein said marker pixel values replace the radiogram pixel densities represented by digital values.

3. The orientation marker according to claim 1 wherein each of said marker pixel values is a unique marker pixel value.

4. The orientation marker according to claim 1 wherein said marker pixels are arrayed along a row and a column and include a marker pixel common to both said row and said column.

5. The orientation marker according to claim 4 wherein the arrayed marker pixels are contiguous.

6. The orientation marker according to claim 4 wherein the radiogram comprises a digital radiographic image and the marker is placed adjacent an upper left hand corner of the digital radiographic image, and wherein the pixel marker common to both the row and column is a first pixel on a first row and a first column of the plurality of rows and column of pixels.

7. A process for identifying a proper orientation of a digital radiogram comprising a plurality of pixels arrayed along rows and columns, each pixel having a digital value representing image densities, the process comprising placing a marker on said image by
   a) selecting a plurality of pixels along at least one row and at least one column to form an array of selected pixels in said radiogram when said radiogram is in said proper orientation;
   b) selecting a plurality of selected digital pixel values;
   c) replacing the digital values of said plurality of selected pixels with said selected digital values to form an asymmetrical array of marker pixels.

8. The process according to claim 7 wherein in step (c) the selected digital values are added to the digital values of said plurality of selected pixels.

9. The process according to claim 7 further comprising:
   d) selecting a plurality of rows and columns to be deleted from the plurality of rows and columns forming the radiogram thereby cropping said radiogram;
   e) identifying any marker pixels in said rows and columns to be deleted and if any are identified; and
   f) relocating all marker pixels to rows and columns in said cropped radiogram whereby said marker pixels in said cropped radiogram are located relative to an edge of said cropped radiogram in a same position as said marker pixels were relative to a same edge of said radiogram prior to cropping.

10. A plurality of digital values representing a radiogram, each of said digital values corresponding to a pixel, and representing said pixel density, wherein a selected number of said digital values are values selected to, in combination with each other, form a machine readable identification code when said radiogram digital values are read in a sequence representing a desired radiogram orientation.

11. The plurality of digital values according to claim 10 wherein said desired orientation is an original orientation.

12. A program storage device readable by a machine, tangibly embodying a program of instructions executable by the machine to perform a set of method steps comprising:
   a) selecting a plurality of pixels along at least one row and at least one column from a plurality of pixels arrayed along rows and columns comprising a radiogram, to form an array of selected pixels in said radiogram when said radiogram is in a first orientation;
   b) retrieving a plurality of selected digital pixel values;
   c) replacing the digital values of said plurality of selected pixels with said selected digital values to form an asymmetrical array of marker pixels.

13. The program storage device according to claim 12 wherein the set of method steps further comprises:
   d) selecting a plurality of rows and columns to be deleted from the plurality of rows and columns forming the radiogram thereby cropping said radiogram;
   e) identifying any marker pixels in said rows and columns to be deleted and if any are identified,
   f) relocating all marker pixels to rows and columns in said cropped radiogram whereby said marker pixels in said cropped radiogram are located relative to an edge of said cropped radiogram in a same position as said marker pixels were relative to a same edge of said radiogram prior to cropping.

* * * * *